United States Patent

Habele

[11] Patent Number: 5,974,919
[45] Date of Patent: *Nov. 2, 1999

[54] SCREWING DEVICE FOR ULTRASOUND-CONTROLLED TIGHTENING OF SCREW CONNECTIONS

[75] Inventor: Michael Habele, Waldenbuch, Germany

[73] Assignee: Robert Bosch GmbH, Stuttgart, Germany

[ * ] Notice: Under 35 U.S.C. 154(b), the term of this patent shall be extended for 199 days.

[21] Appl. No.: 08/513,529

[22] Filed: Aug. 10, 1995

[30] Foreign Application Priority Data

Sep. 6, 1994 [DE] Germany .............................. 44 31 676
Mar. 3, 1995 [DE] Germany ........................... 195 07 391

[51] Int. Cl.⁶ .......................... B25B 23/151; B25B 23/16
[52] U.S. Cl. ......................................... 81/470; 81/177.85
[58] Field of Search ............................ 81/467, 479, 470, 81/177.85

[56] References Cited

U.S. PATENT DOCUMENTS 3,969,810  7/1976  Pagano ..................................... 81/470
4,266,453  5/1981  Farley ................................... 81/177.85
4,535,658  8/1985  Molinari ............................... 81/177.85
4,932,293  6/1990  Goff .................................... 81/177.85
5,448,930  9/1995  Miner et al. .......................... 81/177.85
5,481,949  1/1996  Yen ..................................... 81/177.85

FOREIGN PATENT DOCUMENTS 566987   12/1958  Canada ................................... 81/470
55198    10/1951  France ................................ 81/177.85
1320164   1/1963  France ................................ 81/177.85

*Primary Examiner*—David A. Scherbel
*Assistant Examiner*—Joni B. Danganan
*Attorney, Agent, or Firm*—Michael J. Striker

[57] ABSTRACT

A screwing device provided with a transmission of measuring signals has improved securing of screwing tool. Its rotary drive shaft is connected to the screwing tool in a rotationally locking manner via a polygonal coupling. The screwing tool is fastened axially by two connecting bodies which are arranged in bores and engage in a positively locking manner into an annular groove arranged in the rotary drive shaft in the region of the polygonal coupling. The connecting bodies are retained in their connection position by a securing element.

9 Claims, 4 Drawing Sheets

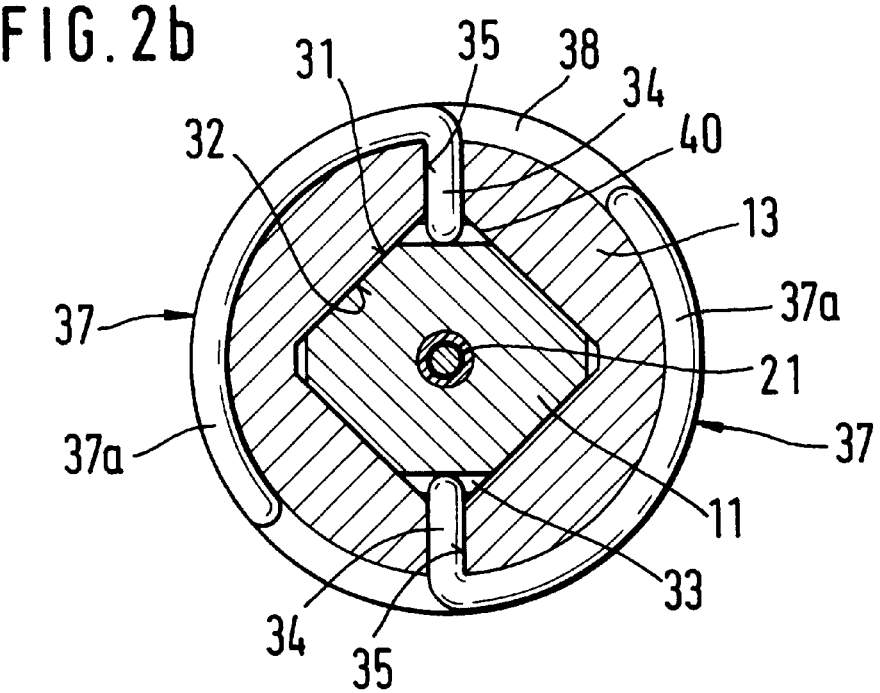
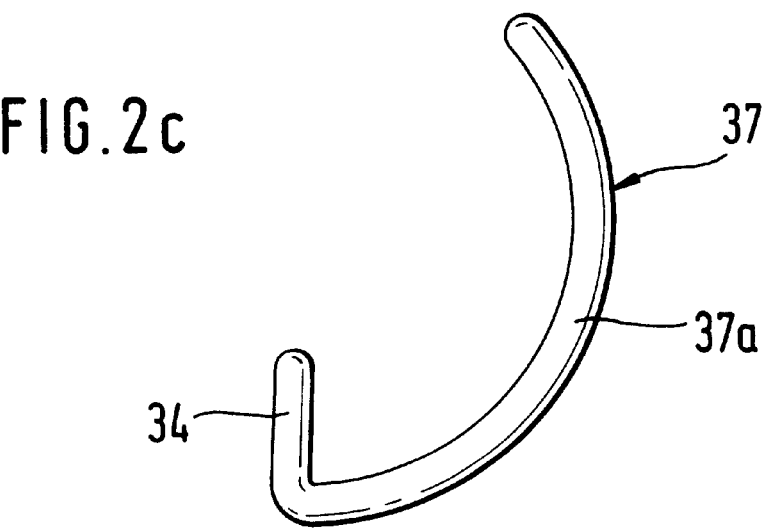

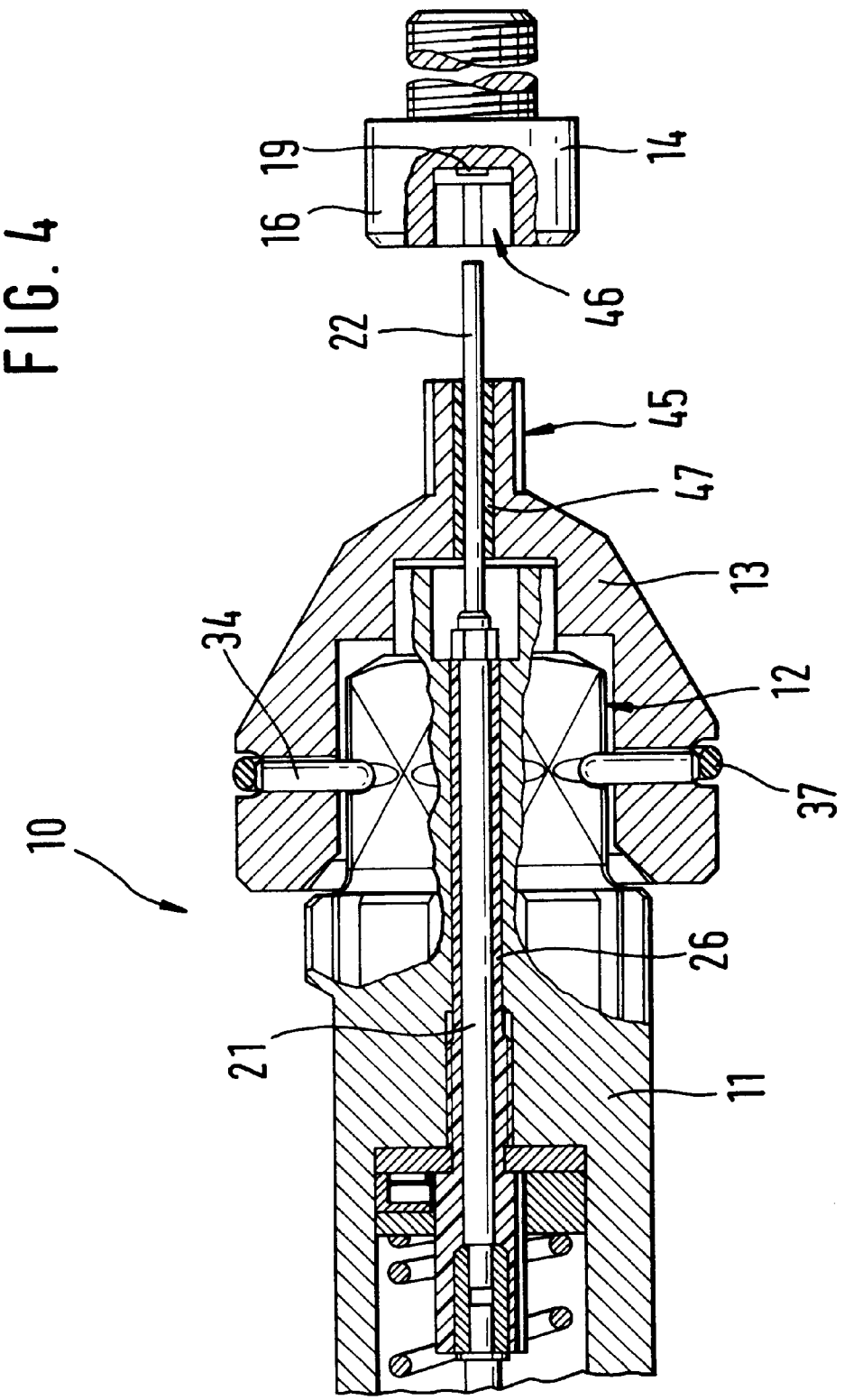

SCREWING DEVICE FOR ULTRASOUND-CONTROLLED TIGHTENING OF SCREW CONNECTIONS

BACKGROUND OF THE INVENTION

The present invention relates to a screwing device for ultrasound-controlled tightening of screw connections.

Screwing devices of the above mentioned general type are known in the art. One such screwing device is disclosed for example in European Patent document 460 920 A1. In the screwing device disclosed in this document a rotary drive shaft is connected in a positively locking manner to a screwing tool via radial pins both in the circumferential direction and in the axial direction. The magnitude of the transmittable torque is limited by the pins, which are subjected to shearing. Furthermore, a simple tool exchange is not possible in the case of the known screwing device.

SUMMARY OF THE INVENTION

Accordingly, it is an object of the present invention to provide a screwing device for ultrasound-controlled tightening of screw connections, which avoids the disadvantages of the prior art.

In keeping with these objects and with others which will become apparent hereinafter, one feature of the present invention resides, briefly stated, in a screwing device for ultrasound-controlled tightening of screw connections, in which a rotary drive shaft and a screwing tool are connectable in a rotationally locking manner via a polygonal coupling with polygonal inserts and corresponding polygonal socket, at least one partially annular groove is provided in the region of the polygonal insert radially on its outer side, at least one bore is provided in the region of the polygonal socket and presses through the wall of the polygonal socket, and connecting body is introduced into the at least one bore, in a connection position of the rotary drive shaft and the screwing tool, engages into the annular groove in a positively locking manner and secured axially in the connection position by a securing element.

When the screwing device is designed in accordance with the present invention, it has the advantage that a higher torque can be transmitted between the rotary drive shaft and screwing tool and a simple tool exchange is, at the same time, made possible.

Particularly advantageous is the design of the screwing tool with a hexagonal insert in the form of a wrench for socket head screws, which is penetrated axially by the transmission element and is insulated electrically with respect to said transmission element by means of an insulating sleeve. The screwing device can thus also be used for screws with a hexagonal socket.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIGS. 2 and 2b show a cross-section along line II—II in FIG. 1;

FIGS. 2a and 2c show views of various securing elements;

FIG. 4 shows a longitudinal section through the tool part of a screwing device according to a fourth exemplary embodiment.

DESCRIPTION OF THE PREFERRED EMBODIMENTS

Figure 1:
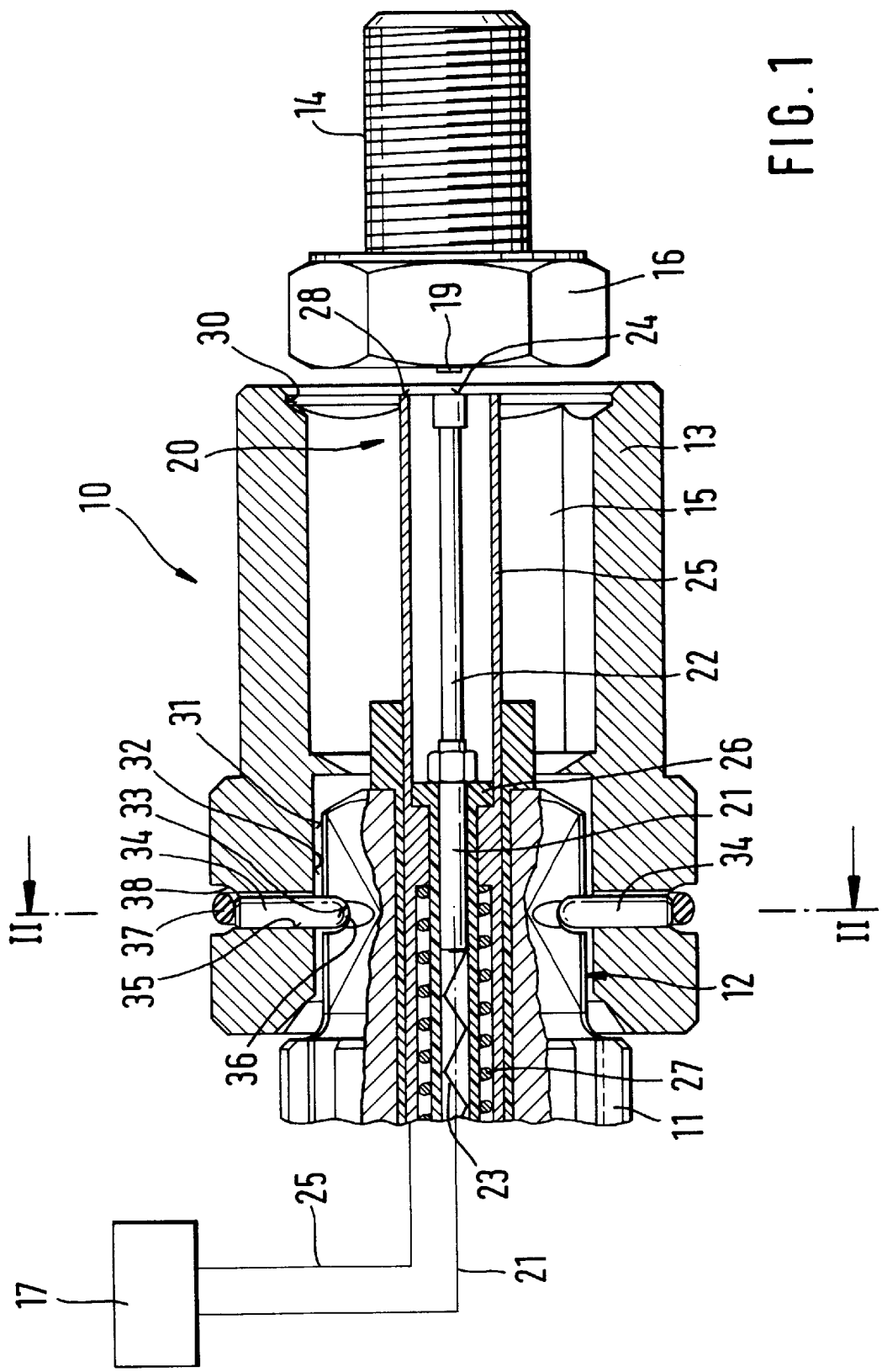
FIG. 1 shows a longitudinal section through a tool part of a screwing device according to a first exemplary embodiment.

FIG. 1, shows a front, tool part of a screwing device. The screwing device 10 is provided with a rotary drive shaft 11 which can be driven in rotation by means of a drive motor (not shown in any more detail). Provided at that end of the rotary drive shaft 11 which is represented in FIG. 1 is a tool-receiving means 12 for a screwing tool 13 which serves for tightening a screw connection. By way of example, all that is shown of the screw connection is a screw 14. However, the screwing device 10 may likewise be attached to a nut of the screw connection. The screwing tool 13 is designed, for example, in the form of a tool nut with a receiving opening 15 which is designed as a hexagonal socket and is intended for a hexagonal screw head 16 of the screw 14.

Located on the end side of the screw head 16 is a vibration body 19, which is vibration-coupled to the screw 14. The vibration body 19 is, for example, a piezoelectric crystal which, with corresponding electric excitation, produces high-frequency acoustic vibrations and conducts the same into the screw connection. Conversely, the piezoelectric crystal receives echo vibrations from the screw connection and converts these into associated echo signals. By comparing excitation signals and echo signals in a schematically represented evaluation device 17, conclusions can be made, in a known manner, as to the voltage state in the screw connection and, consequently, as to the current screwing torque.

The screwing device 10 is provided with means 20 for activating the vibration body 19 and acknowledging the echo signals. The means 20 comprise a transmission element 21 which extends axially, predominantly within the rotary drive shaft 11. At its tool end, the transmission element 21 is designed in two parts with an axially telescopically displaceable contact pin 22 which is formed in the direction of the screw 14 by a spring 23. The transmission element 21 is correspondingly shaped in a hollow-cylindrical manner, with the result that the contact pin 22 can spring in axially therein. Provided at the free tip of the transmission element 21 and/or of the contact pin 22 thereof is a contact surface 24 which serves to activate the vibration body 19, fitted on the screw head 16, and thus comes to bear on the screwing tool 13 when the latter is positioned on the screw 14.

The circuit to the vibration body 19 is closed via an earth conductor 25. The earth connection by way of the earth conductor 25 takes place via the screw head 16, the vibration body 19 being located on the surface thereof. The earth conductor 25 is designed approximately in the form of a sleeve and encloses the contact pin 22 and the transmission element 21 in the front part of the screwing device 10. In this arrangement, the transmission element 21 and the earth conductor 25 are electrically insulated from one another by an insulator 26 and, in the region of the contact pin 22, by a gap.

The earth conductor 25 is axially guided in the rotary drive shaft 11 and can be displaced axially in a resilient manner, as can the contact pin 22. For this purpose, it is forced axially forward by a spring element 27. When the screwing tool 13 is attached to the screw 14, the free end side 28 of the earth conductor 25 makes contact with the electrically conductive screw head 16 at a radial distance from the vibration body 19.

The screwing tool receiving means 12 is designed as a polygonal insert 31, and a corresponding polygonal socket 32, which, in the present example, is of a square design is provided on the screwing tool 13. Of course, the polygonal insert 31 may also, conversely, be formed on the screwing tool 13 and the polygonal socket may be formed on the screwing tool receiving means 12. Together, the polygonal insert 31 and the polygonal socket 32 form a polygonal coupling for transmitting a torque from the rotary drive shaft 11 to the screw connection.

An annular groove 33 is located approximately centrally in the screwing tool receiving means 12. Two connecting bodies 34 engage radially into the annular groove 33. The connecting bodies 34 are each arranged in mutually opposite bores 35 which pass radially through the wall of the screwing tool 13. provision may also be made for fewer or more bores 35 with associated connecting bodies 34, but at least for one bore 35 in which a connecting body 34 can be introduced.

The connecting bodies 34 are designed in the form of pins and are rounded off at their ends 36 engaging into the annular groove 33. In this arrangement, standard pins should be used wherever possible. Upon engagement of the connecting bodies 34 into the annular groove 33, the screwing tool 13 is axially fixed in a positively locking manner on the screwing tool receiving means 12. Radially on the outside, the connecting bodies 34 are overlapped by a securing element 37 and retained in their connection position. In this arrangement, the securing element 37 is designed in the form of a ring, e.g. as an elastic O-ring. The pin-like connecting bodies 34 have play within the bores 35, with the result that, after the securing element 37 has been removed, they can slide out radially outward, the connecting bodies coming out of engagement with the annular groove 33, with the result that the screwing tool 13 can be removed from the rotary drive shaft 11. Provided on the outer circumference of the screwing tool 13, in the region of the bores 35, is an encircling groove 38 in which the securing element 37 is arranged.

Figure 2:
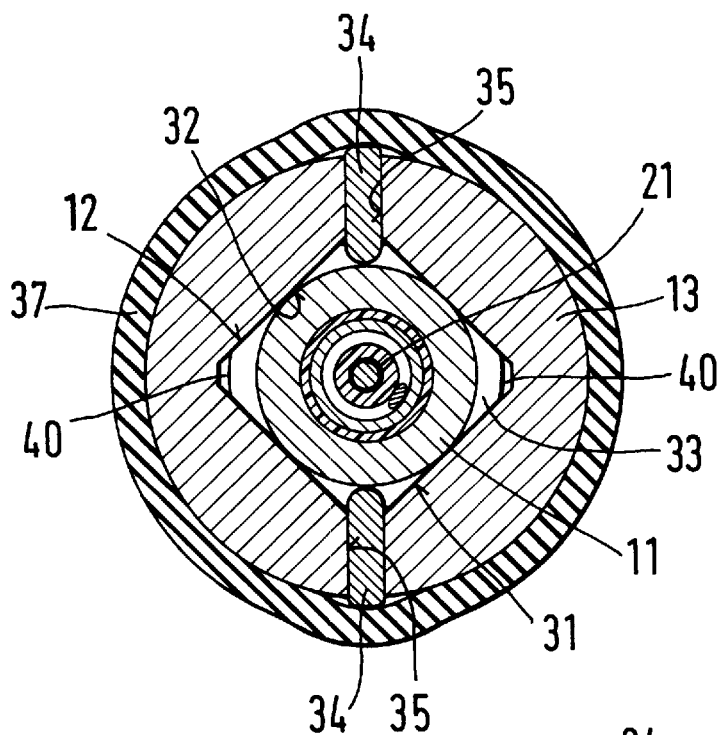

In FIG. 2, the parts used for the connection according to the invention of the rotary drive shaft 11 and screwing tool 13 can be seen in cross-section. The annular groove 33 in the tool receiving means 12 extends merely in the region of edges 40 of the polygonal insert 31 in each case, with the result that the cross-section of the rotary drive shaft 11, and thus the polar resistance torque, is weakened only to an insignificant extent. In any case,the edges 40 do not contribute to any considerable extent to the increase in strength in the event of torsional loading. The bores 35 in the screwing tool 13 are correspondingly arranged in the region of the edges 40 of the polygonal profile 30, with the result that the connecting bodies 34 can engage into the annular groove 33. By virtue of the securing element 37, they are thereby retained in the connection position shown in FIG. 2 such that they cannot be displaced radially outward.

Figure 2A:
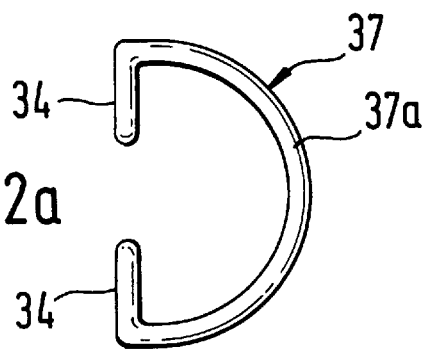

According to the embodiment shown in FIG. 2a on a reduced scale with respect to FIG. 2, the securing element 7 may be formed by a curved member 37a which is in the form of a part-circle, is produced, for example, from spring steel and connects the two connecting bodies 34 at their respectively radially outwardly located ends. Identical and identically acting parts are, as in the case of the following exemplary embodiments, identified by the same reference symbols. For securing position, the curved member 37a can, in the same way as the annular securing element 37 according to the first exemplary embodiment, engage into the encircling groove 38. It goes without saying that the securing element 37 can be produced, together with the connecting bodies 34, from a piece of resilient wire by bending over the ends of the curved member 37a.

The securing element 37 may also, according to FIG. 2c, be designed merely with one connecting body 34. The curved member 37a is bent in the form of a part-circle with a bending radius adapted to the outer radius of the screwing tool 13, and it extends over more than a quarter-arc of a circle. In this manner, the connecting body 34 can be secured in the bore 35 very simply because the connecting body 34 needs only to be plugged into the bore 35, the curved member 37a, which preferably consists of resilient wire, spreading out resiliently and resting, with prestressing, against the outer circumference of the screwing tool 13. According to FIG. 2b, two such securing elements 37 with connecting bodies 34 may also be arranged such that they are offset with respect to one another. The curved member 37a should then extend advantageously over less than a half-arc of a circle. An encircling groove 38 is not absolutely necessary. Such a securing body 37 with connecting body 34 may advantageously be used for securing any screwing tool.

In order also to be able to activate the vibration body 19 when the screwing tool 13 is not positioned fully on the screw head 16, an axial, circular clearance 30 formed, for example, by an encircling incision is provided on that end side of the screwing tool 13 (FIG. 1) which is directed toward the screw 14, said clearance having a greater diameter than the width across the corners of the screw head 16. Consequently, when the edges of the receiving opening 15 and screw head 16 do not coincide, the screw 16 can penetrate into the screwing tool 13 to such an extent that satisfactory electric contact is ensured. This is advantageous in the very case where there is no additional ground conductor 25 and the ground connection takes place via the screwing tool 13 or where ground conductor 25 and contact pin 22 are to be protected and thus, when the screwing tool 13 is removed from the screw head 16, do not project axially beyond the receiving opening 15. In this case, in order to position the screwing tool 13 fully, the edges have to be made to coincide by rotating by means of the screwing drive. When the screwing tool 13 is fully positioned on the screw head 16, the screw head 16 then moves axially forward within the receiving opening during the screwing operation, the advancing contact pin 22 and earth conductor 25 ensuring uninterrupted activation of the vibration body 19.

Figure 3:
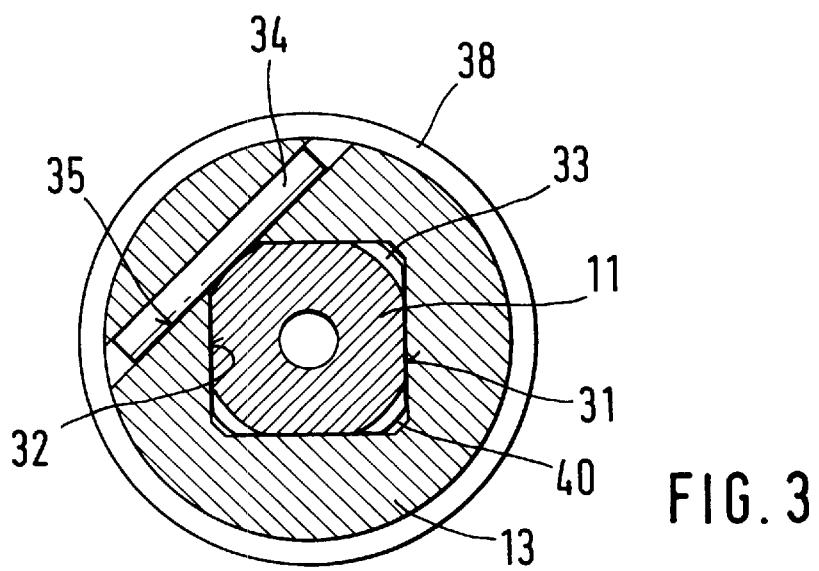
FIG. 3 shows a cross-section through a screwing device according to a third exemplary embodiment.

A third exemplary embodiment of a positively locking connection of rotary drive shaft 11 and screwing tool 13 is shown in FIG. 3. Here too, the rotationally locking connection between the rotary drive shaft 11 and the screwing tool 13 is produced by means of a square. In the polygonal insert 31, which is likewise formed on the rotary drive shaft 11, the annular groove 33 is made in the region of the edges 40. However, all that is provided in the wall of the screwing tool 13 is a bore 35 which runs in the manner of a chord in the tangential direction with respect to the annular groove 33 and intersects one of the four edges 40 such that a connecting body 34 introduced into the bore 35 engages in a positively locking manner into the annular groove 33 and secures the screwing tool 13 on the tool receiving means 12 in a positively locking manner. The connecting body 34 is likewise designed in the manner of a pin. The groove 38 is made on the outer circumference of the screwing tool 13, it being possible, corresponding to the first exemplary embodiment according to FIGS. 1 and 2, for an annular securing element (not shown in FIG. 3), to be arranged in said groove, which securing element retains the connecting body 34 in its connection position.

The fourth exemplary embodiment according to FIG. 4 shows the tool part of a screwing device 10, which is designed essentially as in the case of the first and second exemplary embodiment. However, the screwing tool 13 is provided here with a hexagonal insert 45 in the form of a wrench for a socket head screw, which can be brought into rotationally locking engagement with a corresponding hexagonal socket of a screw 14.

The transmission element 21 fully penetrates the screwing tool 13 in the axial direction with this contact pin 22, which can likewise spring back counter to the spring force. The vibration body 19 is arranged centrally in the base of the hexagonal socket of the screw 14. Contact pin 22 and screwing tool 13 are electrically insulated in the region of the polygonal insert 45 by an insulator sleeve 47.

For space reasons, an earth connection according to the first exemplary embodiment has been dispensed with here. For this purpose of earth conduction, use is made, instead of the above, of the electrically conductive parts comprising screw head 16, screwing tool 13 and rotary drive shaft 11.

It will be understood that each of the elements described above, or two or more together, may also find a useful application in other types of constructions differing from the types described above.

While the invention has been illustrated and described as embodied in a screwing device for ultrasound-controlled tightening of screw connections, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A screwing device for ultrasound-controlled tightening of screw connections, comprising an evaluation device; a vibration body attachable to a head of the screw connection; a rotary drive shaft; at least one axially extending electrical transmission element located in said rotary drive shaft and transmitting signals; a screwing tool for screwing the screw connection and having an axially penetrating receiving opening for receiving said transmission element; a polygonal coupling connecting said rotary drive shaft with said screwing tool in a rotationally locking manner, said polygonal coupling including a polygonal insert and corresponding polygonal socket so that an at least partially annular groove is provided on an outer side of said polygonal insert, said polygonal insert having corners which form outer edges, said polygonal socket being provided with at least one bore which passes through a wall of said polygonal socket; a connecting body insertable in said at least one bore, said connecting body being formed as a pin which in connection position of said rotary drive shaft with said screwing tool engages in said annular groove in a positively locking manner in at least one of said edges; and a securing element which secures said connecting body axially in the connection position.

2. A screwing device as defined in claim 1, wherein said polygonal coupling is substantially square, said polygonal insert being located on said rotary drive shaft while said polygonal socket is located on said screwing tool.

3. A screwing device as defined in claim 1, wherein said securing element is formed at least partially as a ring and rests on an outer side of a circumference of said screwing tool.

4. A screwing device as defined in claim 1, wherein said securing element is formed as a curved member composed of a resilient material and extends over more than a quarter-arc of a circle, said connecting body being formed at one end of said securing element integrally with said securing element.

5. A screwing device as defined in claim 1, wherein said screwing tool in the region of said at least one bore has an at least partially encircling groove for receiving said securing element.

6. A screwing device as defined in claim 5, wherein said securing element is formed as an O-ring.

7. A screwing device as defined in claim 1, wherein said wall of said polygonal socket is provided with an additional bore; and further comprising an additional connecting body extending through said additional bore and formed as a pin, said securing element being formed as a curved member which connects said pins with one another.

8. A screwing device as defined in claim 1, wherein said screwing tool has an end which is remote from said rotary drive shaft and provided with a hexagonal socket formed as a nut, said hexagonal socket being provided on an end side with an axial encircling clearance having a greater diameter than a width across corners of the head of the screw connection.

9. A screwing device as defined in claim 1, wherein said screwing tool is provided with a polygonal insert formed as a wrench for socket head screws.

* * * * *